United States Patent
Gibson et al.

(10) Patent No.: US 7,451,000 B2
(45) Date of Patent: *Nov. 11, 2008

(54) PRE-CURVED COCHLEAR IMPLANT ELECTRODE ARRAY

(75) Inventors: Peter Gibson, Lane Cove (AU); Fysh Dadd, Lane Cove (AU); Claudiu Treaba, Lane Cove (AU); John Parker, Lane Cove (AU)

(73) Assignee: Cochlear Limited, Lane Cove, NSW (AU)

( * ) Notice: Subject to any disclaimer, the term of this patent is extended or adjusted under 35 U.S.C. 154(b) by 679 days.

This patent is subject to a terminal disclaimer.

(21) Appl. No.: 10/332,515

(22) PCT Filed: Nov. 28, 2001

(86) PCT No.: PCT/AU01/01541

§ 371 (c)(1),
(2), (4) Date: Jul. 9, 2003

(87) PCT Pub. No.: WO02/43623

PCT Pub. Date: Jun. 6, 2002

(65) Prior Publication Data

US 2004/0030376 A1    Feb. 12, 2004

(30) Foreign Application Priority Data

Nov. 29, 2000    (AU) .................................... PR1779
Nov. 29, 2000    (AU) .................................... PR1780

(51) Int. Cl.
   *A61N 1/05*    (2006.01)
   *B28B 5/00*    (2006.01)

(52) U.S. Cl. ........................ 607/137; 264/241

(58) Field of Classification Search ......... 607/115–116, 607/55–57, 136–137, 124–126; 29/848, 29/858, 855–856; 600/377, 379, 393; 264/272.11–272.16, 264/239, 241, 263, 299

See application file for complete search history.

(56) References Cited

U.S. PATENT DOCUMENTS 4,357,497 A * 11/1982 Hochmair et al. ............... 607/5

(Continued)

FOREIGN PATENT DOCUMENTS

JP    5-49701    3/1993

(Continued)

OTHER PUBLICATIONS

International Search Report of PCT/AU01/01541, dated Dec. 11, 2001.

(Continued)

*Primary Examiner*—Kennedy J. Schaetzle
*Assistant Examiner*—Jessica Reidel
(74) *Attorney, Agent, or Firm*—Christie, Parker & Hale, LLP (57) ABSTRACT

An implantable electrode array (30) that can adopt a first configuration selected to allow the array (30) to be inserted into a cochlea (12) of an implantee and at least a second configuration in which the array can apply tissue stimulation. The array (30) comprises an elongate carrier (31) having a proximal end (37), a distal end (34), and an inner surface (35) conformable with the inner wall of the implantee's cochlea (12). A plurality of electrodes (36) are supported within the carrier (31) at respective spaced locations thereon in a region between the proximal end (37) and the distal end (34) with at least one of the electrodes having a surface that is at least adjacent the inner surface (35) of the carrier (31). The carrier (31) is formed in the second configuration from a first layer (32) and at least a second layer (32) of resiliently flexible material. A method of forming an array (30) is also described.

16 Claims, 4 Drawing Sheets

U.S. PATENT DOCUMENTS

| | | | |
|---|---|---|---|
| 4,532,930 A | 8/1985 | Crosby et al. | |
| 4,686,765 A | 8/1987 | Byers et al. | |
| 4,819,647 A | 4/1989 | Byers et al. | |
| 5,037,497 A * | 8/1991 | Stypulkowski | 156/245 |
| 5,545,219 A | 8/1996 | Kuzma | |
| 5,578,084 A | 11/1996 | Kuzma et al. | |
| 5,645,585 A | 7/1997 | Kuzma | |
| 5,653,742 A * | 8/1997 | Parker et al. | 607/137 |
| 5,720,009 A | 2/1998 | Kirk et al. | |
| 5,999,859 A * | 12/1999 | Jolly | 607/137 |
| 6,038,484 A | 3/2000 | Kuzma | |
| 6,070,105 A | 5/2000 | Kuzma | |
| 6,078,841 A | 6/2000 | Kuzma | |
| 6,119,044 A | 9/2000 | Kuzma | |
| 6,125,302 A | 9/2000 | Kuzma | |
| 6,144,883 A * | 11/2000 | Kuzma | 607/137 |
| 6,195,586 B1 | 2/2001 | Kuzma | |
| 6,374,143 B1 | 4/2002 | Berrang et al. | |
| 6,397,110 B1 | 5/2002 | Kuzma | |
| 6,421,569 B1 * | 7/2002 | Treaba et al. | 607/137 |
| 6,757,970 B1 * | 7/2004 | Kuzma et al. | 29/847 |
| 2003/0036790 A1 * | 2/2003 | Corbett et al. | 607/137 |
| 2003/0236562 A1 * | 12/2003 | Kuzma | 607/122 |
| 2004/0116995 A1 * | 6/2004 | Dadd | 607/137 |
| 2004/0172118 A1 * | 9/2004 | Gibson | 607/137 |

FOREIGN PATENT DOCUMENTS

| | | |
|---|---|---|
| JP | 10-234866 | 9/1998 |
| JP | 11-502441 | 3/1999 |
| JP | 11-502441 T | 3/1999 |
| WO | WO 93/06698 | 4/1993 |
| WO | WO 97/10784 | 3/1997 |

OTHER PUBLICATIONS

International Preliminary Examination Report of PCT/AU01/01541, dated Sep. 20, 2002.
Corresponding Australian Search Report, dated Jan. 18, 2001.
Patent Abstracts of Japan, Publication No. 05-049701, dated Mar. 2, 1993, in the name of Hiroshi Nakajima et al.
International Search Report for Australian Patent PR3646, dated May 23, 2001, in the name of Cochlear Limited.
Supplemantary Partial European Search Report, dated Apr. 27, 2007, for EP 01998139.8, in the name of Cochlear Limited.

* cited by examiner

PRE-CURVED COCHLEAR IMPLANT ELECTRODE ARRAY

CROSS-REFERENCE TO RELATED APPLICATION

This application is a National Phase Patent Application of International Application Number PCT/AU01/01541, filed on Nov. 28, 2001, which in turn claims priority to Australian Patent Application Number PR 1779, filed on November 29, 2000, and Australian Patent Application Number PR 1780, filed on November 29, 2000.

FIELD OF THE INVENTION

The present invention relates to an implantable device and, in particular, to an implantable cochlear electrode assembly. A method of manufacturing such a device is also described.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

With further improvements in technology becoming available, it is envisaged that in the future it may be possible to provide a cochlear implant that is capable of being totally implanted in an implantee and can operate, at least for a portion of time, without the need for any external devices. Such a device would have an implanted power source and microphone and would be able to perform speech processing functions without the need for an external device and associated link.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

The present invention is directed to an electrode assembly that can preferably be inserted more deeply into the cochlea whilst also preferably reducing the degree of trauma to the sensitive structures within the cochlea. A method of manufacturing such an electrode assembly is also described.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable electrode array that can adopt a first configuration selected to allow the array to be inserted into a cochlea of an implantee and at least a second configuration in which the array can apply tissue stimulation, the array comprising:

an elongate carrier having a proximal end, a distal end, and an inner surface conformable with the inner wall of the implantee's cochlea; and a plurality of electrodes supported within the carrier at respective spaced locations thereon in a region between the proximal end and the distal end, at least one of the electrodes having a surface that is at least adjacent the inner surface of the carrier;

wherein the carrier is formed in said second configuration from a first layer and at least a second layer of resiliently flexible material.

In a first embodiment, each of the electrodes in the array have a surface that is at least adjacent the inner surface of the carrier. In a further embodiment, the surfaces of the electrodes are aligned with the inner surface of the carrier. In another embodiment, the surfaces of the electrodes stand proud of the inner surface of the carrier. It is also envisaged that the electrode surface could also be recessed into the inner surface of the carrier.

In a first embodiment, the first layer can overlay each of the electrodes except their said respective surfaces adjacent the inner surface of the carrier. The first layer preferably extends for at least a portion of the length of the carrier. The first layer can extend from the proximal end to the distal end of the carrier. The second layer also preferably extends for at least a portion of the length of the carrier. The second layer can also extend from the proximal end to the distal end of the carrier.

In a further embodiment, the second layer can overlay at least a portion of an outer surface of the first layer. The second layer can overlay a majority of the outer surface of the first layer, and still more preferably can overlay the entire outer surface of the first layer.

In one embodiment, the first layer and second layer can be formed from different materials. In another embodiment, the first and second layers can be formed from the same material. In one embodiment, the first and second layers can each be formed from a medical grade, biocompatible elastomeric material. In one embodiment, the elastomeric material can be a silicone rubber. In another embodiment, tile elongate member can be formed from a polyurethane or similar material.

In a further embodiment, the thickness of the first layer between its inner surface and outer surface can be substantially constant for at least a majority of its length from the proximal end to the distal end. In another embodiment, the thickness of the first layer can change, such as decrease, from the proximal end to the distal end. In a further embodiment, the thickness of the second layer can be constant for at least a majority of its length. In a still further embodiment, the thickness of the second layer can change, such as decrease, from the proximal end to the distal end.

In a still further embodiment, the thickness of the second layer can be substantially the same as the first layer. It can, however, be envisaged that the thickness of the second layer may be greater than or less than the diameter of the first layer of the carrier.

In one embodiment, the second layer is bonded to the first layer. The bonding can be provided by an adhesive layer or can be achieved by bringing the layers together while in a state that results in bonding together of the respective layers.

In a preferred embodiment, the implantable electrode array is a cochlear implant electrode array, with the carrier being adapted for insertion into the cochlea of an implantee. Preferably, the carrier is adapted for insertion into the scala tympani of the cochlea of the implantee.

In a preferred embodiment, the second configuration of the carrier is preferably a curved configuration. Preferably, the curved configuration is such that the carrier can fit inside the cochlea of the implantee with said adjacent surfaces of the electrodes being oriented to face the modiolus of the cochlea.

The outer surface of the second layer of the carrier is preferably smooth to prevent any damage to the cochlea as the carrier is inserted into the cochlea.

In a further embodiment, the carrier can have a lumen extending longitudinally from an opening at the proximal end into the carrier. The lumen can extend to a position close to the distal end of the carrier. The lumen can be positioned in the first layer or the second layer. In another embodiment, the lumen can be positioned between the first and second layers.

The lumen can be cylindrical or have any other suitable cross-sectional shape. The proximal opening of the lumen can be closable by a closure means adapted to seal the opening of the lumen.

The electrode array can be provided with a stiffening element that is sized to fit into the lumen and extend substantially through the carrier. When the stiffening element is within the lumen, the carrier can be biased into a first, substantially straight, configuration in which the carrier is insertable into the cochlea of the implantee.

In a preferred embodiment, the lumen has a cross-sectional dimension which decreases as the elongate carrier changes shape from the substantially straight first configuration to a curved configuration to allow, if desired, the stiffening element to be withdrawn.

The stiffening element can comprise a stylet formed from a malleable and biocompatible material. The stylet can be formed from a suitable metal, such as platinum, or a metallic alloy or relatively stiff plastics material.

In another embodiment, the stiffening element can be formed from a bioresorbable material which softens or dissolves on exposure to a fluid. The stiffening element can soften or dissolve on exposure to a saline solution or a body fluid of the implantee, such as cochlear fluid.

In a further embodiment, the bioresorbable material of the stiffening element is selected from the group consisting of polyacrylic acid (PAA), polyvinyl alcohol (PVA), polylactic acid (PLA) and polyglycolic acid (PGA). It is envisaged that other similar materials could also be used.

In a still further embodiment, the stiffening element can be formed from a shape memory material. For example, the stiffening element can be formed from a nickel-titanium alloy or Nitinol™ and shaped to take a straight or substantially straight configuration at room temperature but bends into another shape on exposure to body temperature.

In a further embodiment, the stylet can include a tip, the tip being more flexible than the remainder of the stylet.

The carrier can also include a tip member, the tip member being straighter than the rest of the elongate carrier. The tip member is also preferably more flexible than the remainder of the stylet. In a further embodiment, the stylet can have a variable stiffness.

In a preferred embodiment, the electrode array can include electrically conducting wires connected to the electrodes and extending to at least said proximal end. In one embodiment, one wire can be connected to each of said electrodes. In another embodiment, at least to wires can be connected to each of said electrodes.

Each electrode can comprise a contact member. The carrier can have a longitudinal axis with each contact member arranged orthogonally to the longitudinal axis. The contact members can be formed from a biocompatible material. The biocompatible material can be platinum. The wires are preferably connected to the contact members by welding.

The carrier of the electrode array preferably naturally adopts a spiral configuration. In a preferred embodiment, the spiral carrier subtends an arc greater than 450°.

In yet a further embodiment, the lumen in the carrier can act as a substance delivery means for delivering a bio-active substance to the implant site following implantation. In an alternative embodiment, another lumen can be formed in the carrier to act as the substance delivery means.

The lumen can act as a reservoir for the bio-active substance. In one embodiment, the bio-active substance in the reservoir can leach from the lumen into the surrounding material of the carrier and eventually migrate to an outer surface of the carrier, such as the inner surface of the first layer, that is preferably close to the desired site of action for the bio-active substance. In another embodiment, the carrier can have one or more substance egress means whereby the bio-active substance can move out of the lumen and through the carrier to a position that is preferably close to the desired site of action for the bio-active substance.

Where the bio-active substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen within the carrier.

In a further embodiment, the proximal opening of the lumen can be in fluid communication with an additional reservoir for the bio-active substance that is external to the carrier. A pumping means, such as an osmotic pump, can transfer the bio-active substance from the additional reservoir into the lumen of the carrier for subsequent delivery to the appropriate site of action.

It is also envisaged that the bio-active substance can be captured in the form of a solid pellet. An example of how this may occur is by impregnating the bio-active substance in a ceramic or a polymer pellet that has a predetermined rate of release of the bio-active substance. This solid pellet can then be stored in the lumen reservoir or in an external reservoir connectable to the lumen.

In another embodiment, a stiffening element made from a bioresorbable material can also be impregnated with one or more of the bio-active substances allowing the stiffening element to perform a dual role. The rate of delivery of the bio-active substance can be programmed by design of the element structure.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation.

In a still further embodiment, at least a portion of the outer surface of the carrier can have a coating of lubricious material. In a further embodiment, a substantial portion of the outer surface can have a coating of the lubricious material. In a still further embodiment, the entire outer surface of the carrier can have a coating of the lubricious material.

The lubricious material preferably becomes lubricious on being brought into contact with a fluid, such as a saline solution. Still further, the coating preferably becomes lubricious on being brought into contact with a body fluid, such as cochlear fluid.

In one embodiment, the lubricious material is selected from the group consisting of polyacrylic acid (PAA), polyvinyl alcohol (PVA), polylactic acid (PLA) and polygiycolic acid (PGA). It is envisaged that other similar materials could also be used. It is envisaged that the lubricious material can also be impregnated with the bio-active substance allowing the coating to perform a dual role. The rate of delivery of the bio-active substance can be programmed by design of the coating structure.

In a still further embodiment, the carrier can be enveloped by a stiffening sheath which is made of a material that is relatively stiffer than the resiliently flexible material of the carrier. The stiffening sheath can be adapted to bias the carrier into a substantially straight configuration. In one embodiment, the stiffening sheath can be overlaid by the coating of lubricious material.

Where both the stiffening element and stiffening sheath are present in the device, the element and sheath can be adapted in combination to bias the carrier into the substantially straight configuration. In this embodiment, if either the stiffening element or the stiffening sheath is removed or deactivated, the carrier can adopt at least one intermediate configuration. In this embodiment, the stiffening sheath can be formed of the same material or a different material to that of the stiffening element. In either case, the stiffening sheath can be relatively more stiffer or relatively less stiffer than the stiffening element.

The stiffening sheath, if present, can be formed of a bioresorbable material which dissolves or softens on exposure to a fluid. The stiffening sheath can dissolve or soften on exposure to a saline solution or a body fluid of the implantee, such as cochlear fluid and in doing so also release one or more bioactive substances impregnated therein.

In a further embodiment, the bioresorbable material of the stiffening sheath is selected from the group consisting of polyacrylic acid (PAA), polyvinyl alcohol (PVA), polylactic acid (PLA) and polyglycolic acid (PGA). It is also envisaged that other suitable materials could also be used. It is envisaged that the bioresorbable element of the stiffening sheath can also be impregnated with one or more bio-active substances allowing the stiffening sheath to perform a dual role. The rate of delivery of the bio-active substance can be programmed by design of the sheath structure.

The carrier can include an additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer. In this embodiment, the coating of lubricious material can be coated on the outside of the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment at least one slit can allow a different rate of progress of fluid through the additional layer compared to the other slits.

The stiffening sheath, if present, can be formed from a shape memory or heat sensitive material. For example, the stiffening sheath can be formed from a nickel-titanium alloy or Nitinol™ and shaped to take and maintain the straight or substantially straight configuration of the carrier at room temperature but bends it into another shape once it is exposed to body temperature.

In one embodiment, while both the stiffening element and the stiffening sheath are in position within the carrier, it will retain the first substantially straight configuration. If the stiffening sheath is removed or softened, whether it is by dissolution or otherwise, the remaining stiffening element can have insufficient strength to retain the carrier in its first configuration. It is preferred that the carrier, on removal or softening of the stiffening sheath, will adopt an intermediate configuration in which the carrier has at least some curvature.

The present invention provides a surgeon with a cochlear implant electrode array that can potentially be inserted to a greater degree than hitherto known electrode arrays whilst maintaining close proximity between the surfaces of the electrodes and the modiolus.

According to another aspect, the present invention is an implantable electrode array for insertion into the cochlea of an implantee, said array comprising:

a first layer made of a resiliently flexible material and supporting a plurality of electrodes within said first layer with at least one of said electrodes having a surface that is at least adjacent the inner surface of the first layer, said first layer being of a curved configuration;

at least a second layer made of resiliently flexible material and overlaying an outer surface of the first layer, said at least second layer also being of a curved configuration;

wherein the plurality of layers together form a pre-curved electrode carrier capable of applying tissue stimulation.

In this aspect, the degree of curvature of the first layer is greater than that of the at least second layer.

The degree of curvature of the electrode carrier can be controlled by altering one or both of the degrees of curvature of the first and at least second layers.

Each of the electrodes in the first layer have a surface that is at least adjacent the inner surface of the carrier.

In another aspect, the present invention is an implantable electrode array for insertion into the cochlea of an implantee, said array comprising:

a first layer made of a resiliently flexible material and having a curved configuration and a first degree of curvature;

at least a second layer made of a resiliently flexible material and having a curved configuration and a second degree of curvature;

wherein the layers in combination form an electrode array having a degree of curvature dependent on the respective degrees of curvature of the first layer and the at least second layer.

In this aspect, the first layer has a greater degree of curvature than the at least second layer.

According to a further aspect, the present invention is a method of manufacturing an implantable electrode array, the method comprising the steps of:

(i) moulding a first layer of an elongated carrier from a resiliently flexible material about a longitudinal array of electrodes such that at least one of the electrodes has a surface that is at least adjacent an inner surface of the carrier; and (ii) moulding a second layer of the carrier from a resiliently flexible material over at least a portion of the surface of the first layer other than its inner surface.

In a preferred embodiment, the electrodes can comprise a plurality of rings. The formed carrier can have a longitudinal axis with each electrode arranged orthogonally to the longitudinal axis. The electrodes can be formed from a biocompatible material, such as platinum. The electrode array is preferably formed by positioning a series of platinum rings on or about a longitudinal support that is preferably removable once the carrier has been moulded about the electrodes. The support can comprise a wire that is coated with a low-friction material, such as polytetrafluroethylene (PTFE).

Once positioned about the PTFE-coated wire, a series of electrically conducting wires can be welded to each of the electrodes. Each electrode preferably has at least one, and more preferably two, electrically conducting wires welded thereto.

Once the electrodes are positioned about the PTEE-coated wire, the array is placed in a first mould to allow formation of the first layer. In a preferred embodiment, the carrier is adapted for insertion into the cochlea. As such, it is preferred that the array is placed in a spiral-shaped mould. The spiral-shaped mould preferably subtends an arc of greater than 720°. The mould is preferably specifically adapted to form a first layer of the carrier in which the spiral shape of the first layer subtends an arc greater than the carrier ultimately formed by the method when the second layer is moulded thereto.

The first layer is preferably formed from an elastomeric silicone material and remains in the first mould until cured.

Once cured, the formed first layer of the carrier is removed from the first mould. The first layer can then be placed in a second mould having a set of dimensions generally greater than the first mould. In the case of a cochlear implant array, the second mould again preferably comprises a spiral-shaped mould. The second mould typically subtends an arc less than that of the first mould. In one embodiment, the second mould subtends an arc of about 180° less than the arc subtended by the first mould.

On placement of the first layer in the second mould, the inner surface of the first layer is preferably adapted to abut with the inner surface of the second mould. Given that the first layer has been formed in a first mould having smaller dimensions and a relatively tighter degree of curvature, the first layer will preferentially abut the inner surface of the second mould. This serves to ensure that the electrodes that are positioned adjacent the inner surface are not coated with a layer of elastomeric material when the second layer is moulded to the first layer in the second mould.

The second layer is preferably formed from a elastomeric silicone material, with the carrier remaining in the second mould until the second layer is cured. The second layer can be formed from the same material as the first layer or a different material.

Once the second layer is cured, the carrier can be removed from the second mould and straightened. The carrier may be straightened by and held straight in a straightening jig.

Once at least substantially straightened, the PTFE-coated wire can be gently removed from within the carrier. The removal of the PTFE-coated wire results in the formation of a lumen within the first layer of the carrier.

If desired, while still being held at least substantially straight, a straightening element, such as a metallic stylet or non-metallic stylet-like member can be inserted into the lumen to hold the carrier in the straightened configuration until such time, as the carrier is to be inserted into a cochlea.

In a still further aspect, the present invention is an implantable electrode array when formed using the method of the further aspect defined above.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
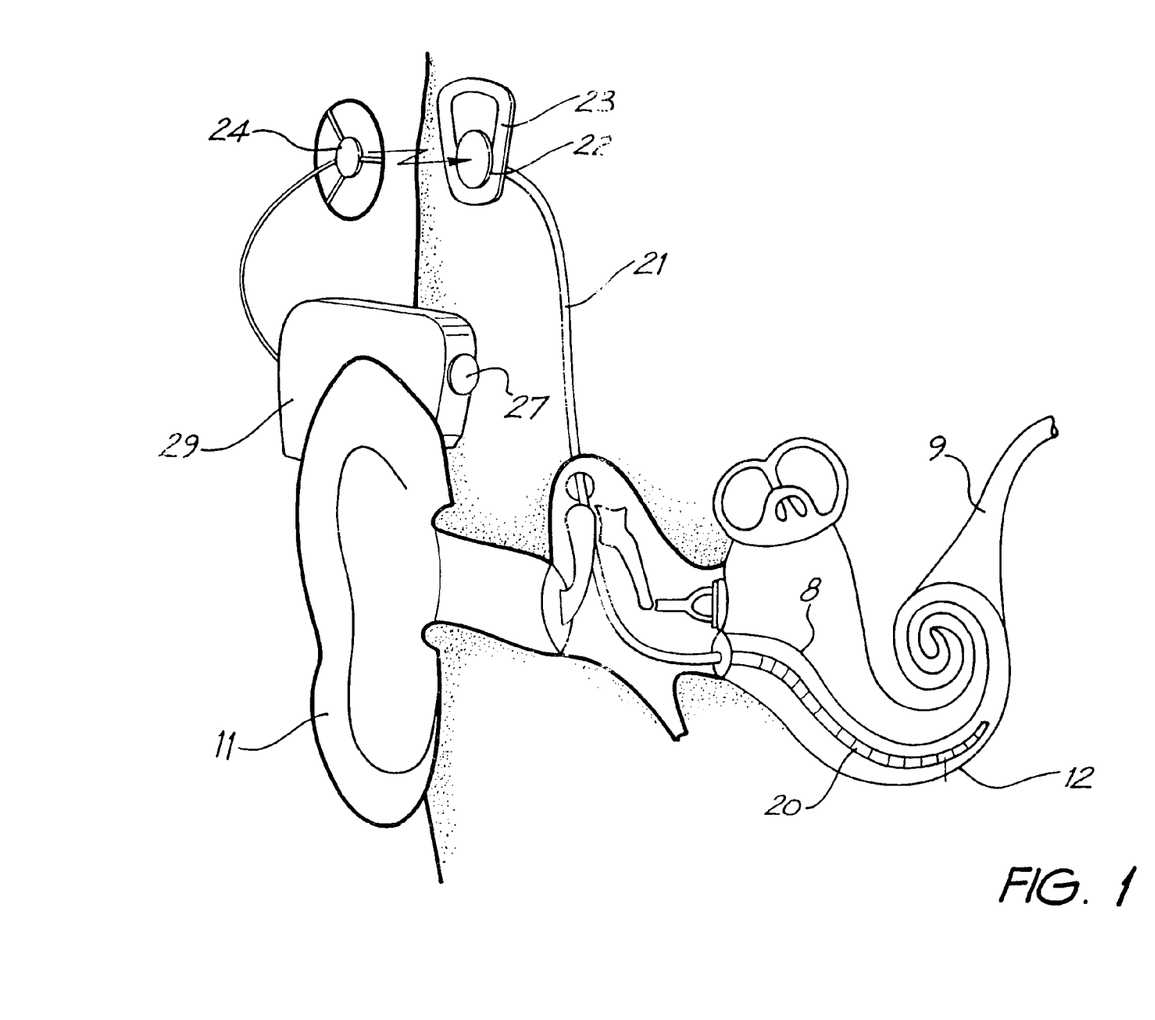
FIG. 1 is a simplified pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

As depicted diagrammatically in FIG. 1, the cochlear implant electrode array 20 has traditionally been inserted into the initial portion of the scala tympani of the cochlea 12, and typically up to about a full turn within the cochlea. The electrode array according to the present invention is adapted to be inserted more deeply into the cochlea 12 than has historically been the case. For the purpose of the remainder of the specification, one embodiment of a cochlear implant electrode array is depicted generally as 30 in FIG. 5.

Figure 5:
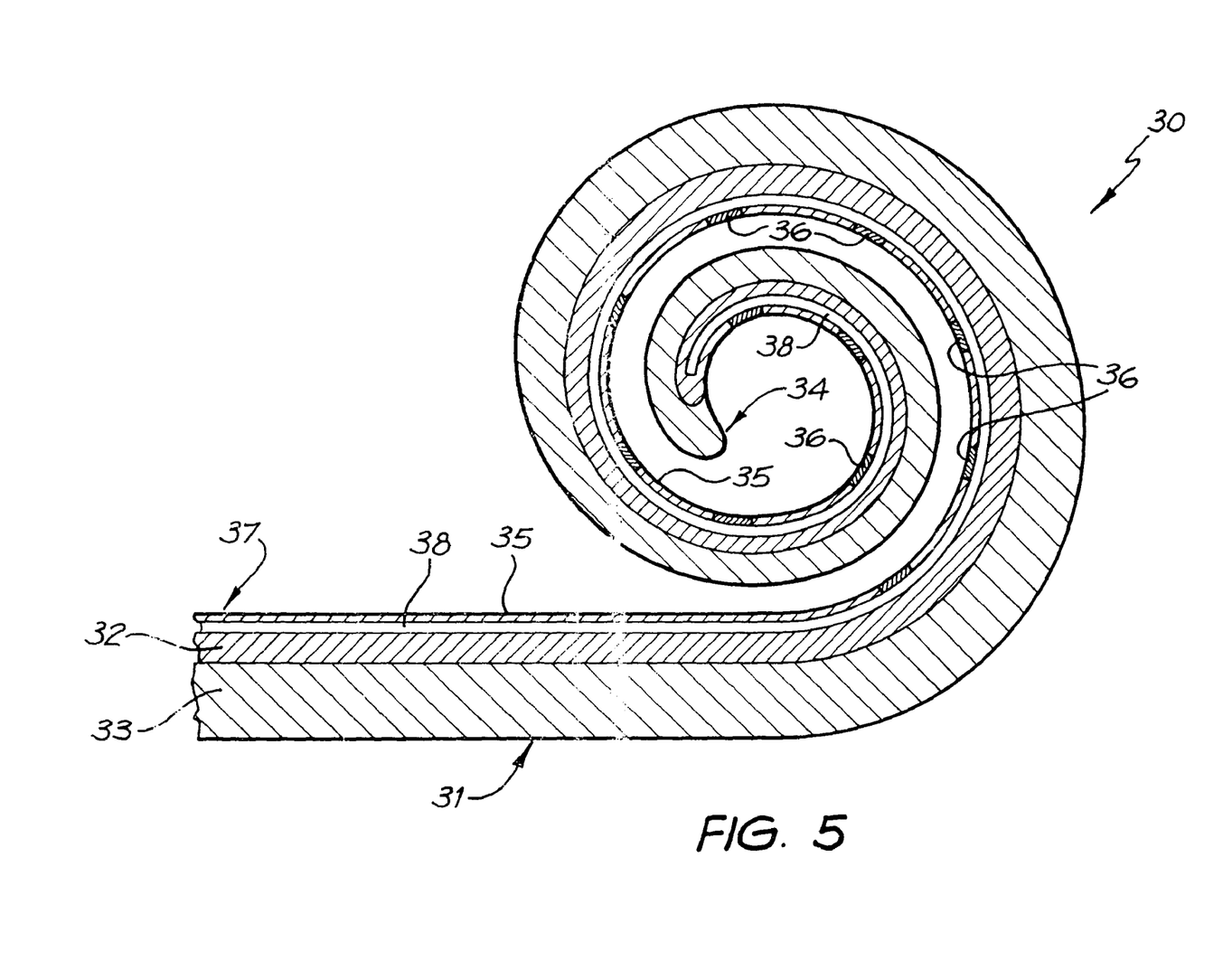
FIG. 5 is a cross-sectional view of an elongate carrier for a cochlear implant electrode array according to the present invention having both a first and second layer.

The array 30 comprises an elongate electrode carrier member 31. The depicted elongate member 31 is preformed from a first layer 32 and a second layer 33 of resiliently flexible silicone with memory and is formed in a curved configuration suitable for placement in the scala tympani of a human cochlea 12. In the depicted embodiments, each layer 32,33 is formed from the same elastomeric silicone material. It will be understood by a person skilled in the art that the layers 32,33 could be formed from different materials to one another should a particular characteristic of the material be desired.

The elongate member 31 has a first distal end 34 that is firstly inserted into the cochlea 12 upon insertion of the array 30. The elongate member also has an inner surface 35 adapted to be positioned at least close to the surface of the modiolus of the cochlea 12 following insertion of the array 30. Disposed within the first layer are a plurality of electrodes 36. It will be appreciated that the electrodes 36 depicted in FIG. 5 are not necessarily drawn to scale.

Further, more or less electrodes than that depicted in FIG. 5 could be utilised in the elongate member 31. Each electrode 36 comprises a platinum contact surface having an outer surface at least adjacent, and preferably substantially aligned with, the inner surface 35 of the first layer 32 of the elongate member 31. While not depicted, it will be understood that at least one electrically conducting wire would extend from each of the electrodes 36 through the elongate member 31 to at least the depicted end 37 of the member 31. The wires would normally extend back to an implanted stimulator/receiver unit, such as unit 22 depicted in FIG. 1.

Disposed longitudinally through the first layer 32 is a lumen 38. It may also be possible to have more than one lumen extending longitudinally through the array 30. The lumen 38 can have a number of uses. While depicted in the first layer 32, the lumen could extend longitudinally through the second layer 33 or even further, a lumen could be provided in both layers, 32 and 33. It could also be positioned at the longitudinal join between the first and second layers 32,33.

The lumen 38 can have disposed therein, prior to insertion of the assembly 30 into the cochlea 12, a substantially straight platinum stylet. The stylet can have a stiffness that is sufficient to retain the silicone elongate member 31 in a straight configuration. It will be appreciated that the stylet could be constructed so as to have a stiffness that was insufficient alone to retain the elongate member 31 in a straight configuration.

Instead of a platinum stylet, a bioresorbable stylet-like member formed from a bioresorbable polyacrylic acid (PAA) which is adapted to dissolve or soften on exposure to cochlear fluids, could be utilised with appropriate modification to the elongate carrier member 31. A stiffening polymer stylet could also be utilised. Both such embodiments of a polymeric stylet could also be impregnated with a bio-active substance.

A bioresorbable stylet would preferably soften quickly, but not dissolve quickly, with its very slow dissolution rate allowing any impregnated bioactive substance to effectively elute to the body.

Whilst a substantially cylindrical lumen is depicted, the lumen 38 could be any shape necessary to perform the function.

If used, a stylet-like member from a bioresorbable material can have a stiffness that is either sufficient or insufficient to retain the silcone elongate member 31 in a straight configuration. It will be appreciated that a bioresorbable stylet-like member could be formed from other suitable bioresorbable materials. A stylet-like member made from a shape memory material could also be utilised instead of a platinum stylet.

While the depicted elongate member 31 is manufactured in a curved configuration, the array 30 is typically delivered to a surgeon in a sterile package with a stylet or stylet-like member in place.

On removal from the package and insertion into the scala tympani of the cochlea 12, the platinum stylet can be withdrawn to allow the elongate member 31 to commence to adopt its naturally curved configuration, with the electrodes 36 facing the modiolus within the cochlea 12 so that they are positioned as close as possible to the spiral ganglia thereof.

The provision of a cochlear implant electrode array 30 having a first and second layer 32,33 allows the elongate member 31 to be inserted, in a typical case, more deeply into the scala tympani of the cochlea 12 than would be the case for hitherto traditionally used arrays, such as array 20 depicted in FIG. 1.

Figure 2:
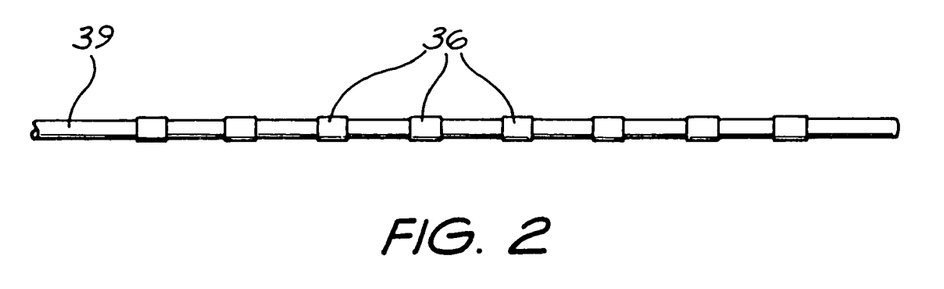
FIG. 2 is a plan view of PTFE-coated wire having a plurality of platinum ring electrodes mounted thereon.

To form the electrode array 30 depicted in FIG. 5, a plurality of platinum rings, which become the electrodes 36, are mounted on a PTEE-coated wire 39. While not depicted, each ring 36 has preferably at least two conductive wires welded thereto to allow electrical connection from the implanted stimulator/receiver unit 22 to the rings 36.

Figure 3:
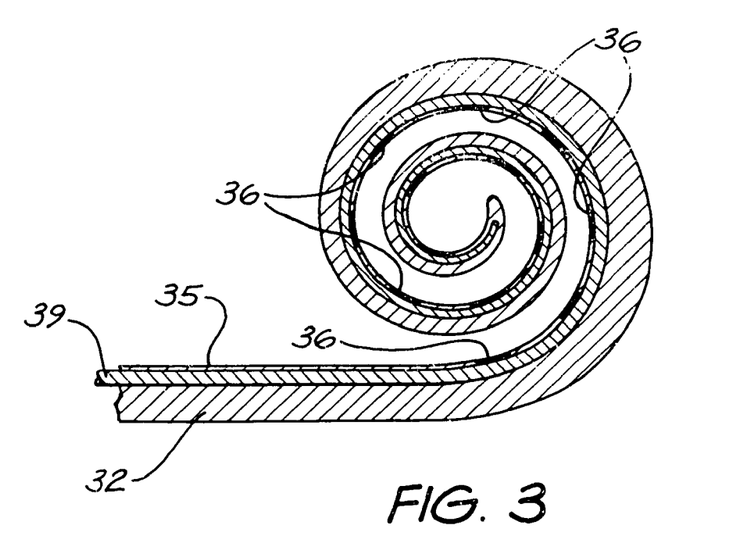
FIG. 3 is a sectional view of a first layer of an elongated carrier according to the present invention.

Once formed, the electrode assembly depicted in FIG. 2 is placed in a first spiral-shaped mould, with the outer surfaces of the rings 36 abutting the inner surface thereof. The spiral of the first mould preferably subtends an arc of greater than 720°. Once correctly positioned in the first mould, a silicone is poured/injected into the first mould around the wire 39 and allowed to cure. Once cured, the formed elastomeric first layer 32 can be removed from the first mould. As depicted in FIG. 3, the PTFE-coated wire 39 is preferably left in place following removal from the first mould.

Figure 4:
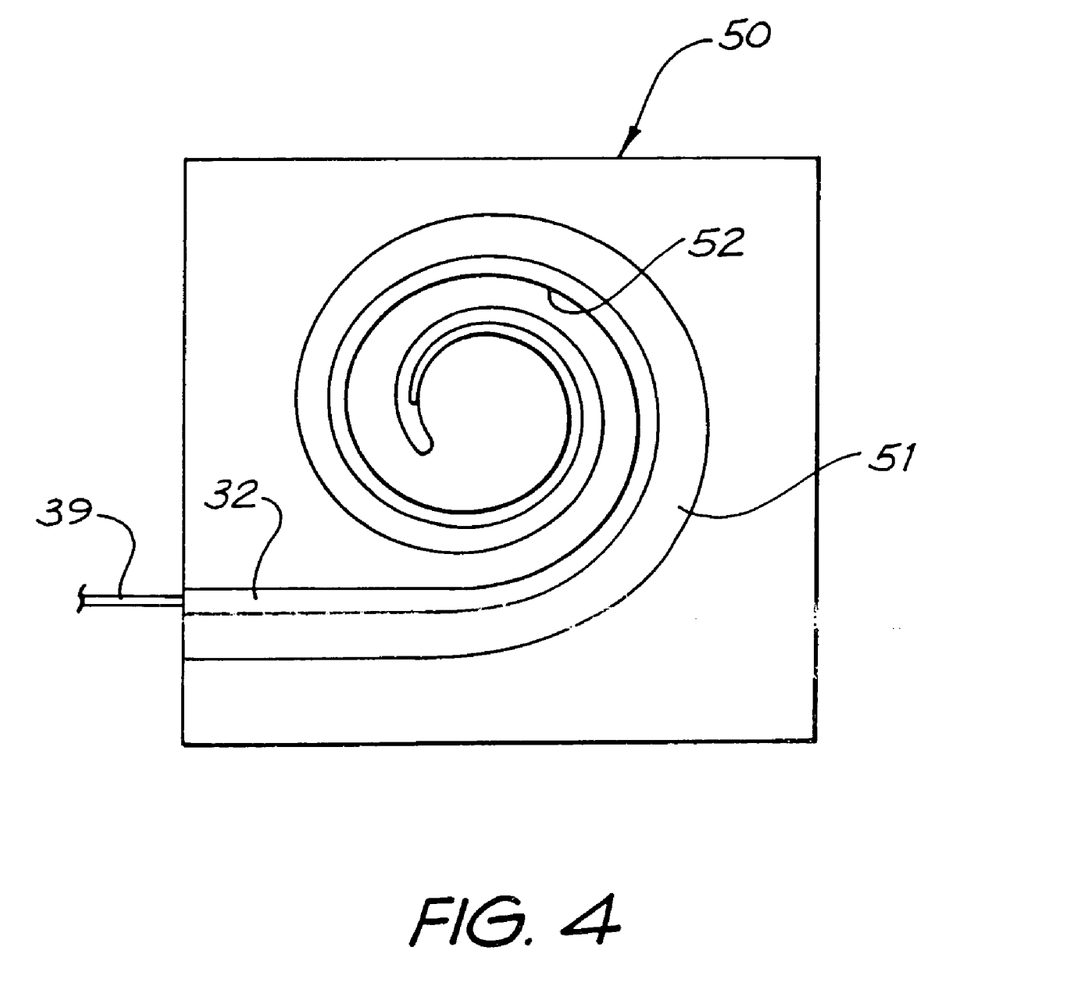
FIG. 4 is a plan view depicting the first layer of FIG. 3 positioned in a second mould ready for moulding of the second layer of the carrier.

Once removed from the first mould, the first layer 32 can be positioned in a second mould, such as the spiral mould 50 depicted in FIG. 4. The mould 50 has a spiral-shaped channel 51 formed therein. The channel 51 subtends an arc that is about 180° less than the arc subtended by the equivalent channel in the first mould (not depicted).

As the relaxed condition of the first layer 32 has a tighter degree of curvature than the curvature of the channel 51, the inner surface 35 of the first layer 32 abuts with the inner surface 52 of the channel 51 on being placed therein.

Once positioned in the second mould 50, a further quantity of silicone can be poured/injected into the mould and allowed to cure. The further quantity of silicone forms the second layer 33 of the elongate member 31 depicted in FIG. 5.

Once the second layer is cured, the elongate member 31 can be removed from the second mould 50. If desired, the elongate member 31 can then be placed in a straightening jig before the PTFE-coated wire 39 is removed from the member 31. The removal of the wire 39 leaves a longitudinal lumen 38 in the first layer 32 as already described herein.

The use of a two-step process as defined herein results in the formation of an elongate member having a greater degree of curvature than hitherto known in traditional cochlear implant electrode arrays. Further to this, the use of a two-step process of the present invention allows for the width and thickness of the electrode array to be more easily modified to provide for a thinner array if desired.

While the preferred embodiment of the invention has been described in conjunction with a cochlear implant, it is to be understood that the present invention has wider application to other implantable electrodes, such as electrodes used with pacemakers and the like.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of manufacturing an implantable electrode array comprising a carrier having a first layer and at least a second layer, the method comprising the steps of:
    moulding the first layer of the carrier in a first spiral-shaped mould having a first degree of curvature from a first resiliently flexible material about a series of electrodes such that at least one of the electrodes has a surface that is at least adjacent an inner surface of the first layer;
    removing the first layer from the first mould, once the first layer is at least partially cured and placing the first layer in a second spiral-shaped mould having a second degree of curvature different from the first degree of curvature; and
    moulding the second layer of the carrier from a second resiliently flexible material over at least a portion of the surface of the spiral-shaped first layer other than its inner surface.

2. A method of manufacturing an implantable electrode array of claim 1 wherein the series of electrodes is formed by positioning a series of platinum rings on or about a removable longitudinal support.

3. A method of manufacturing an implantable electrode array of claim 2 wherein the support comprises a wire coated with a relatively low-friction material.

4. A method of manufacturing an implantable electrode array of claim 3 wherein once the electrodes are positioned on or about the wire, at least one electrically conducting wire is welded to each of the electrodes.

5. A method of manufacturing an implantable electrode array of claim 3 wherein the first spiral-shaped mould subtends an arc of greater than about 720°.

6. A method of manufacturing an implantable electrode array of claim 3 wherein the second degree of curvature of the second spiral-shaped mould is less than the first degree of curvature, said second mould comprising a spiral-shaped cavity having at least an inner surface and which subtends an arc less than that of the first mould.

7. A method of manufacturing an implantable electrode array of claim 6 wherein the second mould subtends a spiral arc of about 180° less than the spiral arc subtended by the first mould.

8. A method of manufacturing an implantable electrode array of claim 7 wherein on placement of the first layer in the second mould, the inner-surface of the first layer abuts with the inner surface of the second mould.

9. A method of manufacturing an implantable electrode array of claim 8 wherein once the second layer is at least partially cured, the carrier is removed from the second mould and placed in a straightening jig.

10. A method of manufacturing an implantable electrode array of claim 9 further comprising removing the wire from within the carrier so leaving a lumen within the carrier.

11. A method of manufacturing an implantable electrode array of claim 1 wherein first resiliently flexible material is the same as the second resiliently flexible material.

12. A method of manufacturing an implantable electrode array comprising a carrier having a first layer and at least a second layer, the method comprising the steps of:
moulding the first layer of the carrier in a first spiral-shaped mould having a first degree of curvature from a resiliently flexible material about a series of electrodes such that at least one of the electrodes has a surface that is at least adjacent an inner surface of the first layer; and
in a second spiral-shaped mould, moulding the second layer of the carrier from the resiliently flexible material over at least a portion of the surface of the spiral-shaped first layer other than its inner surface, wherein the second spiral-shaped mould has a second degree of curvature different than the first degree of curvature.

13. A method of manufacturing an implantable electrode array of claim 12 wherein the series of electrodes is formed by positioning a series of platinum rings on or about a removable longitudinal support.

14. A method of manufacturing an implantable electrode array of claim 13 wherein the support comprises a wire coated with a relatively low-friction material.

15. A method of manufacturing an implantable electrode array of claim 14 wherein once the electrodes are positioned on or about the wire, at least one electrically conducting wire is welded to each of the electrodes.

16. A method of manufacturing an implantable electrode array of claim 12 wherein the second degree of curvature is less than the first degree of curvature.

* * * * *